(12) United States Patent
Murray et al.

(10) Patent No.: US 11,114,019 B2
(45) Date of Patent: Sep. 7, 2021

(54) HARDWARE-BASED GRAPHICS INTERFACE FOR MEDICAL DEVICE SENSORS AND CONTROLLERS

(71) Applicant: Valcura Medical, Inc., San Bruno, CA (US)

(72) Inventors: Patrick C. Murray, San Diego, CA (US); Jorge E. Martinez-Vargas, Jr., San Francisco, CA (US); Owen K. Jones, Middletown, RI (US); Steven L. Gardner, Damascus, OR (US)

(73) Assignee: Valcura Medical, Inc., San Bruno, CA (US)

( * ) Notice: Subject to any disclaimer, the term of this patent is extended or adjusted under 35 U.S.C. 154(b) by 0 days.

(21) Appl. No.: 17/146,016

(22) Filed: Jan. 11, 2021

(65) Prior Publication Data

US 2021/0248949 A1     Aug. 12, 2021

Related U.S. Application Data

(60) Provisional application No. 62/975,161, filed on Feb. 11, 2020.

(51) Int. Cl.
*G06F 13/14*     (2006.01)
*G09G 3/20*     (2006.01)
(Continued)

(52) U.S. Cl.
CPC ....... *G09G 3/2092* (2013.01); *A61M 16/0051* (2013.01); *A61N 1/08* (2013.01);
(Continued)

(58) Field of Classification Search
CPC .......... G06F 3/14; G09G 5/363; G09G 5/006; G09G 1/001; G06T 1/20
(Continued)

(56) References Cited

U.S. PATENT DOCUMENTS 4,898,169 A * 2/1990 Norman ................... A61B 1/31
                                                                       606/42
8,131,380 B2   3/2012   Cao et al.
(Continued)

OTHER PUBLICATIONS

"Definitions of Hardware, Software, and Firmware for Digital Logic Systems", A Scientific Study of the Problems of Digital Engineering for Space Flight Systems, with a View to Their Practical Solution, Available Online at: http://klabs.org/ce_watch/definitions/hw_sw_definitions.htm, Aug. 6, 2009, 3 pages.

*Primary Examiner* — Gordon G Liu
(74) *Attorney, Agent, or Firm* — Kilpatrick Townsend & Stockton LLP

(57) ABSTRACT

A completely hardware-based graphics interface controller for reading values from sensors or outputting voltages, currents, or other electrical parameters to medical devices is proposed. The graphics interface controller accepts analog or digital input into a programmable logic device (PLD), whose logic gates convert the input value to memory addresses of bitmaps that represent digits or other characters. The bitmaps are copied to respective x, y coordinates in a frame buffer, which are then displayed on a matrix liquid crystal display (LCD) panel. The bitmaps can be simple or elaborate, mimicking the rich look and feel of general purpose computer fonts so that the display output is compelling and modern-looking despite being entirely hardware based. A ventilator or other medical device can be instrumented with one or more sensors whose outputs are to the graphics interface, and an alarm can be triggered for off-nominal conditions.

22 Claims, 6 Drawing Sheets

(51) Int. Cl.
  *G16H 20/40*   (2018.01)
  *A61N 1/08*   (2006.01)
  *A61M 16/00*   (2006.01)

(52) U.S. Cl.
  CPC .......... *G09G 3/2085* (2013.01); *G16H 20/40* (2018.01); *A61M 2205/502* (2013.01); *G09G 2380/08* (2013.01)

(58) Field of Classification Search
  USPC ........................................................ 345/520
  See application file for complete search history.

(56) References Cited

U.S. PATENT DOCUMENTS

| | | | |
|---|---|---|---|
| 2002/0099477 A1* | 7/2002 | Wallace | G06F 9/453 700/299 |
| 2002/0154082 A1* | 10/2002 | Zavracky | G06F 1/1662 345/88 |
| 2007/0139024 A1* | 6/2007 | Zolfaghari | G05F 1/575 323/273 |
| 2016/0287470 A1* | 10/2016 | Lewis | A61B 5/361 |
| 2018/0365350 A1* | 12/2018 | Anue | G06F 30/327 |
| 2019/0117057 A1 | 4/2019 | Knox | |

* cited by examiner

HARDWARE-BASED GRAPHICS INTERFACE FOR MEDICAL DEVICE SENSORS AND CONTROLLERS

CROSS-REFERENCES TO RELATED APPLICATIONS

This application claims priority from U.S. Patent Application No. 62/975,161, filed Feb. 11, 2020, which is hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

The present application generally relates to interface circuits for specific input/output devices including sensors and displays. Specifically, an all-hardware based logic circuit parses and translates analog voltages and currents or serial digital data from a sensor into memory addresses of bitmaps. The bitmaps are pictures of human-readable digits. The bitmaps of digits are displayed at their appropriate place values on a specific matrix liquid crystal display (LCD) panel.

2. Description of the Related Art

Graphical displays are becoming increasingly popular due to mass use in everyday life, and product users are expecting a graphical user interface (GUI) for everything from banking applications to medical devices. The mass use of graphical displays has led to the innovation and development of display modules that are cheaper to produce while also being feature-rich.

Due to rapid innovation and development, the integration of display modules are generally not sustainable long term since there could be problems with sourcing components required for the design due to manufacturers' obsoleting previous products while upgrading to keep up with the latest technological developments. Typically, product suppliers in the medical device industry may not be able to afford to redesign their products in order to keep up with rapid innovation seen in consumer electronics. Because products look old without modern GUIs, users are hesitant to purchase certain equipment that does not meet their constantly increasing expectations.

The medical device industry has the added burden of complying with health and safety regulations that subject devices to regulatory scrutiny and approval. Software can be especially difficult to certify, and sometimes it may be subject to hacking. Thus, integrating a fresh-on-the-market display module that incorporates new software into an existing medical device takes a great deal of time and resources.

There is a need in the art for better graphics interfaces for medical equipment that meet graphical quality expectations of end users and minimize the burden of certification.

BRIEF SUMMARY

Generally, a completely hardware-based graphics interface for matrix liquid crystal display (LCD) panels is disclosed in which signals from one or more sensors or external sources are parsed and fed through pre-burned logic circuits of a programmable logic device (PLD) that output addresses of bitmaps that were pre-saved in memory. Each bitmap is like a flash card; it shows a nicely drawn digit, such as '0,' '1,' '2,' etc. It is copied wholesale to a display buffer memory at a predefined x, y coordinate appropriate for the place value of the digit and shown on the LCD panel. In this way, a modern-looking GUI on an LCD display is presented without requiring software.

Such a user interface, which does not require any software, can be incorporated more easily in medical devices. For example, it allows for the display and control of real-world voltages and currents in galvanic current generator to treat hemorrhoids. The hardware-based graphics controller and current generator can code and decode analog or digital signals while maintaining concurrent galvanic current control to a therapeutic device. The hardware-based graphics controller includes a logic device configured to code and decode digital signals for a graphical user interface while also managing the use of a surgical pencil medical device. Generally, the controller may include a timer, a current source and conditioning circuit to generate an current output, an ammeter to measure the output current, a liquid crystal display (LCD), and a memory that are operatively coupled to the logic device.

This disclosure also relates to the hosting of pixel representation of specific images in the memory, i.e., bitmaps, to allow a logic device to select the specific pixel representations from memory based on specific designated inputs such as but not limited to the timer, the current output, and the ammeter reading. It can also extend to the authentication of a unique code interrogated from an external device such as a surgical pencil that allows the logic device to perform certain actions based on the authentication of the unique code. Generally, the controller apparatus will be user driven based on the treatment needs of a hemorrhoid patient who requires hemorrhoidolysis. Thus, the galvanic current supplied through the connection port of an exemplary surgical pencil medical device can be managed during a hemorrhoid treatment procedure.

Some embodiments of the invention are related to a hardware-based display apparatus for medical devices, the apparatus including a sensor input, a matrix liquid crystal display (LCD) panel, a read-only memory (ROM) hosting two-dimensional, graphical bitmaps of digits 0 through 9, each bitmap stored at a predetermined, fixed memory location within the ROM, a programmable logic device (PLD) operatively connected with the display panel and the ROM, the PLD configured to automatically convert a value from the sensor input, through a series of logic gates, to at least one selected location of the ROM memory locations storing the bitmaps of digits, and copy the bitmap from the selected location to a frame buffer address corresponding to an x, y coordinate on the display panel, wherein the display panel is configured to show the bitmap that is copied to the frame buffer address at the x, y coordinate.

The automatically converting can include converting the value from the sensor input to an integer or floating point number within the PLD. The PLD can be further configured to compare the integer or floating point number to a threshold and trigger an alarm based on the number exceeding the threshold. The PLD can be further configured to copy, based on the trigger, a graphic from the ROM to a second frame buffer address corresponding to a second x, y coordinate on the display panel. The apparatus can further include a speaker, wherein the PLD is further configured to sound, based on the trigger, an audible alarm through the speaker. A speaker can include an audio speaker, buzzer, or electronic audible device. The apparatus can further include a timer, wherein the PLD is further configured to trigger the alarm based on the number exceeding the threshold over a time period clocked by the timer.

The PLD can be further configured to parse the value from an RS-232 serial stream, a universal serial bus (USB) data packet, or inter-integrated circuit (I²C) packet from the sensor input. The PLD can be further configured to convert the value from an analog voltage or analog current from the sensor input. The apparatus can further include a sensor coupled to the sensor input.

Embodiments can include an alarmed ventilator comprising the hardware-based display apparatus, a pneumatic valve assembly including a housing with a fluidic input port configured to receive pressurized gas into the housing, a diaphragm within the housing, an adjustable knob configured to adjust force against the diaphragm, and a pressure sensor within the housing coupled to the sensor input, wherein the hardware-based display apparatus is configured to show a value from the pressure sensor.

The frame buffer address can be on a random-access memory (RAM) that is on a separate chip from the PLD. The apparatus can further include a serializer-deserializer (SerDes) configured to read from the frame buffer address and transmit pixel values to the display panel. The frame buffer associated with the frame buffer address could be configured so that it only addresses a subset of x, y pixel areas of the display panel.

The PLD can be a programmable read-only memory (PROM), erasable programmable read-only memory (EPROM), electrically erasable programmable read-only memory (EEPROM), flash memory EPROM, field programmable gate array (FPGA), programmable array logic (PAL), programmable logic array (PLA), application specific integrated circuit (ASIC), or application specific standard product (ASSP), among other programmable logic devices.

Some embodiments relate to a hardware-based graphics controller and therapeutic electric current generator apparatus including a timer, a current source with a conditioning circuit and an output, an ammeter configured to measure the current source output, a liquid crystal display (LCD), a programmable logic device (PLD) connected with the timer, the ammeter, and the LCD, a read-only memory operatively connected with the PLD, the memory hosting two-dimensional pixel representations of digits 0 through 9, icons, or other graphics, a fixed image address on the LCD for displaying time, and a permanent image address on the LCD for displaying current, wherein the PLD is configured to select pixel representations from the memory based on values from the timer and write the selected pixel representations starting at the fixed image address, and wherein the PLD is configured to look up pixel representations from the memory based on values from the ammeter and write the looked-up pixel representations starting at the permanent image address.

The apparatus can further include an interrogation circuit configured to read an authentication code from a connected device and allow current to flow from the current source only if the authentication code is legitimate. The interrogation circuit can be further configured to prevent current flowing from the current source after a predetermined number of readings of the authentication code. The connected device can be a surgical pencil or a return electrode.

The apparatus can further include a user-selectable switch for increasing or decreasing electrical current from the current source, the PLD configured to adjust the timer based on operation of the switch. The current source and the conditioning circuit can be configured to output direct current (DC) at a selected value up to 50 milliamps while keeping a ripple voltage below ±500 millivolts. The current source and conditioning circuit can be limited to output DC at a maximum of 25 milliamps, thereby suitable for negative galvanism of hemorrhoids

DETAILED DESCRIPTION

Figure 1:
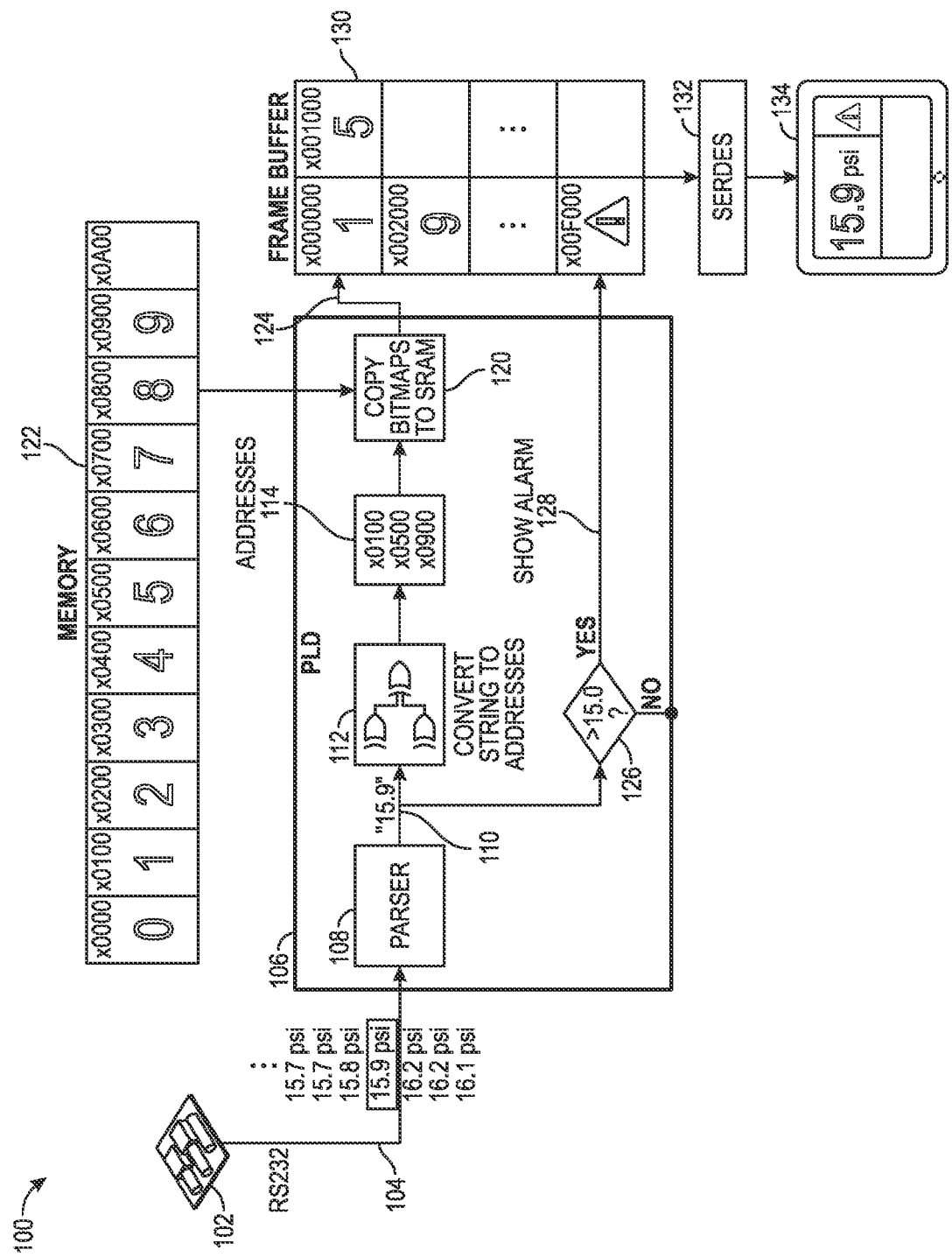
FIG. 1 illustrates a hardware-based graphics interface fed by RS232 data in accordance with an embodiment.

A hardware-based graphics interface that can be used with matrix liquid crystal display (LCD) panels is presented. Instead of having software, firmware is burned into a programmable logic device (PLD)—in which the circuit connections are unchanged during operation. The PLD decodes signals and copies "flash card" bitmaps of pre-drawn digits, characters, symbols, or other graphics to the display. Because the graphics interface does not rely upon software for operation, certification of software may be avoided.

The hardware-based graphics controller apparatus that may be coupled with medical devices such as an anoscope, a surgical pencil, and/or grounding pad or return electrode for the treatment of hemorrhoids within an anal or rectal cavity. In some embodiments, the described hardware-based graphics controller may include a timer, a current source, an ammeter, a liquid crystal display (LCD), a programmable logic device (PLD) or logic device, and a read-only memory. In some embodiments, the described read-only memory may include a memory hosting a two-dimensional pixel representations of digits that may be selected and displayed at a predetermined fixed address on the LCD by a PLD configured to select the pixel representations from memory and write the pixel representations to a permanent image address.

A "liquid crystal display (LCD) panel" (without the "matrix" adjective) includes all passive & active, segmented & matrix, and monochrome & color electronic displays using liquid crystal technology, or as otherwise known in the art. This includes those displays having simple 7-segment digits, 14- or 16-segment characters, n×m matrices of pixels. It includes twisted nematic (TN), supertwisted nematic (STN), film compensated STN (FSTN), double layer STN (DSTN), enhanced STN (ESTN), intelligent STN (ISTN), and thin film transistor (TFT) LCDs. It includes non-backlit or backlit LCD displays using fluorescent light, light emitting diode (LED), or other backlight technologies.

A "matrix LCD display panel" (with the "matrix" adjective) includes displays with an array of pixels in columns and rows, typically with capability to turn all of the individual pixels on or off independently, or as otherwise known in the art. This distinguishes the display from custom design and segmented-digit readouts in which predefined shapes and/or symbols are permanently fashioned into the LCD instead of pixels.

Video Graphics Array (VGA) resolution is 640 by 480 pixels, monochrome or color, and was a common standard for matrix LCD panels. As an early standard, many graphics drivers and displays accommodate VGA resolution as a standard graphics mode. VGA resolution is often a lower bound threshold for displays that are large enough to be considered to have enough area for matrix created graphics.

A "programmable logic device" (PLD) includes a programmable read-only memory (PROM), erasable programmable read-only memory (EPROM), electrically erasable programmable read-only memory (EEPROM), flash memory EPROM, field programmable gate array (FPGA), programmable array logic (PAL), programmable logic array (PLA), application specific integrated circuit (ASIC), application specific standard product (ASSP), or other programmable logic devices as known in the art. Distinct from a general purpose computer that fetches an instruction from memory into a current instruction register and then executes the instruction to output data to one or more accumulators, a PLD employs a set of distributed logic circuits whose physical structure normally does not change while processing.

FIG. 1 illustrates a hardware-based graphics interface fed by RS232 digital serial data. In system 100, carbon dioxide ($CO_2$) sensor 102 sends digital data 104 across RS232 line 104 into programmable logic device (PLD) 106. The PLD includes parser 108 that parses the RS232 data to pick out a relevant string of data 110. The string of data represents a value from the RS232 data.

Data string 110 is then fed through converter 112 to convert the numeric characters to a set of addresses 114. At each address in memory 122 pointed to by the set of addresses, a bitmap whose data represents a picture of a digit, letter, or other character or symbol, exists. The bitmap is a sort of flash card that shows a graphical representation of the character. For example, an address can contain a vertical line and serifs to indicate the number '1.' The bitmap can be nicely drawn in a crisp font so as to mimic what is available on general purpose computers and printers, but without the need for an operating system (OS) or all of the other overhead of a general purpose computer or printer.

A blank bitmap may be reserved for cases in which no digit or character should be shown in a particular position. For example, for numbers less than one hundred, a hundreds column may show a blank bitmap rather than a leading zero so that it is more natural to read. Similarly, round integers may forgo displaying a zero after a decimal point and instead show a blank bitmap.

The bitmap is copied from memory 122 by memory accesser 120 to static random-access memory (SRAM) frame buffer 130. Frame buffer 130 can include all the pixels in a complete video frame on the display like a traditional frame buffer or only hold a subset of the pixels.

Meanwhile, data string 110 is converted to a floating point number using other logic gates, and the number is compared in comparator logic 126 to a threshold. If the number is beyond the threshold (i.e., above, equal to, or below depending on the type of threshold), then a flag 128 to show an alarm is set. If flag 128 is set, then a warning symbol or other character is copied to the frame buffer 130.

"Exceeding a threshold" includes having a value greater than a maximum threshold value, having a value less than a minimum threshold value, or as otherwise known in the art.

In some embodiments, the flag triggers a display element that is not part of the matrix to appear, such as a warning symbol above, below, or to the side of other matrix elements.

Some bitmaps are not selected based on the input to parser 108 but rather always shown. For example, a colon in between minutes and seconds on a clock, units such as '° C.,' or text such as "Elapsed Time" can be permanently copied to or set within the frame buffer so that they will be shown all of the time.

Serializer/deserializer (SerDes) 132 takes pixel data from frame buffer 130 and transfers it to display panel 134 for presentation. The various bitmaps are shown in their respective positions. At no point from the input of the RS232 data to the presentation on the display was software used. Rather, the parsing, decoding, looking up of addresses, copying, and input into the frame buffer was all done by fixed logic gates in a PLD. Similarly, triggering the alarm also did not proceed through software.

Figure 2:
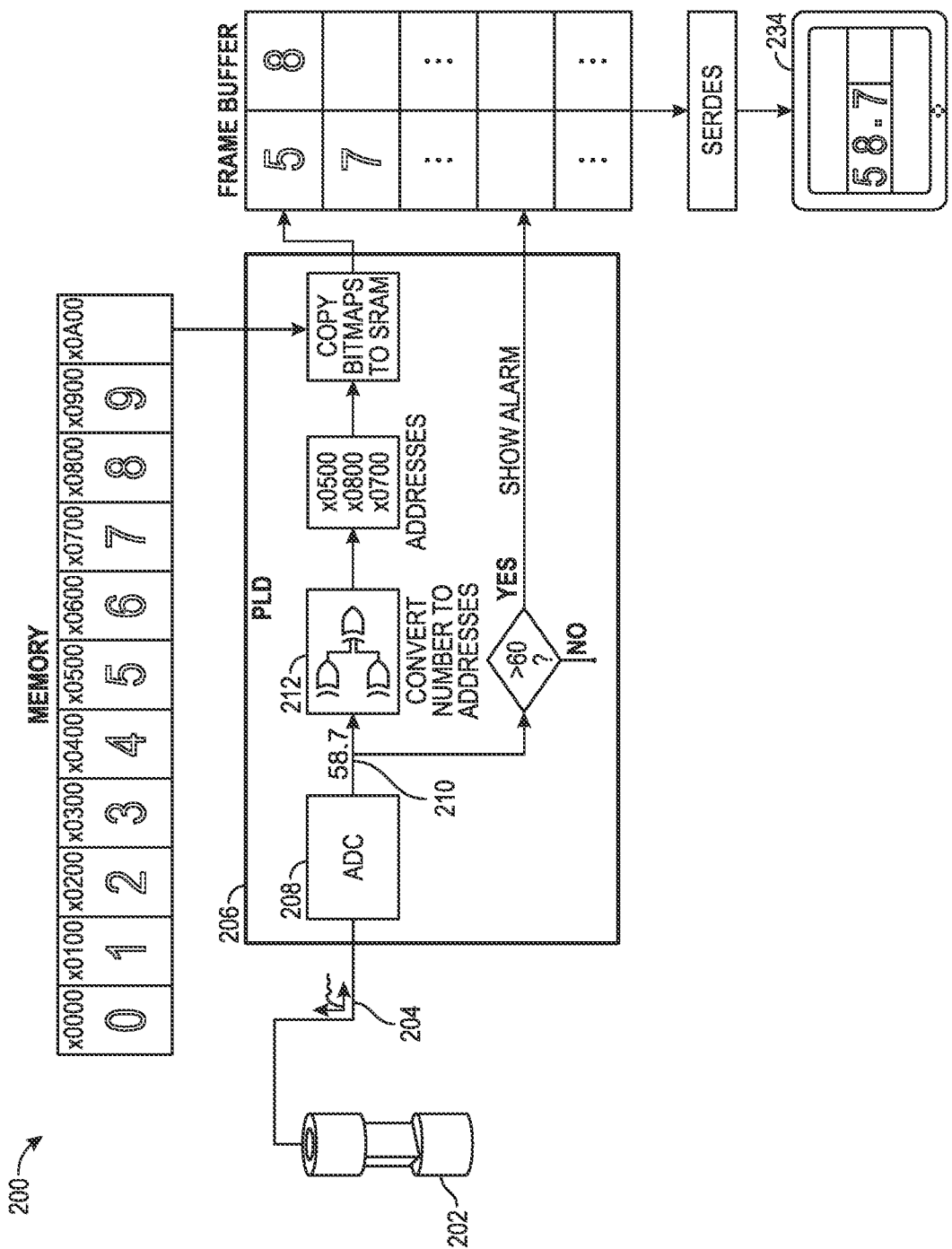
FIG. 2 illustrates a hardware-based graphics interface fed by an analog sensor in accordance with an embodiment.

FIG. 2 illustrates a hardware-based graphics interface fed by an analog sensor. There are many parallels with the implementation of FIG. 1, yet the PLD in this embodiment accepts analog voltages or current. Other embodiments may also accept analog voltages or current but with analog-to-digital converters that are separate from the PLD.

In system 200, flow meter 202 outputs analog voltage 204 that represents a mass flow of a gas. PLD 206 includes built-in analog-to-digital converter (ADC) 208. ADC 208 reads analog voltage 204 and outputs a digital value, floating point number 210. Floating point number 210 is a digital representation of the voltage or mass flow from flow meter 202.

The floating point number is fed through logic gates 212 in order to determine addresses of bitmaps of digits that should be displayed on the screen of display panel 234. Similarly, the floating point number is compared in order to determine whether an alarm icon should be shown or an audible alarm sounded through a speaker.

Figure 3:
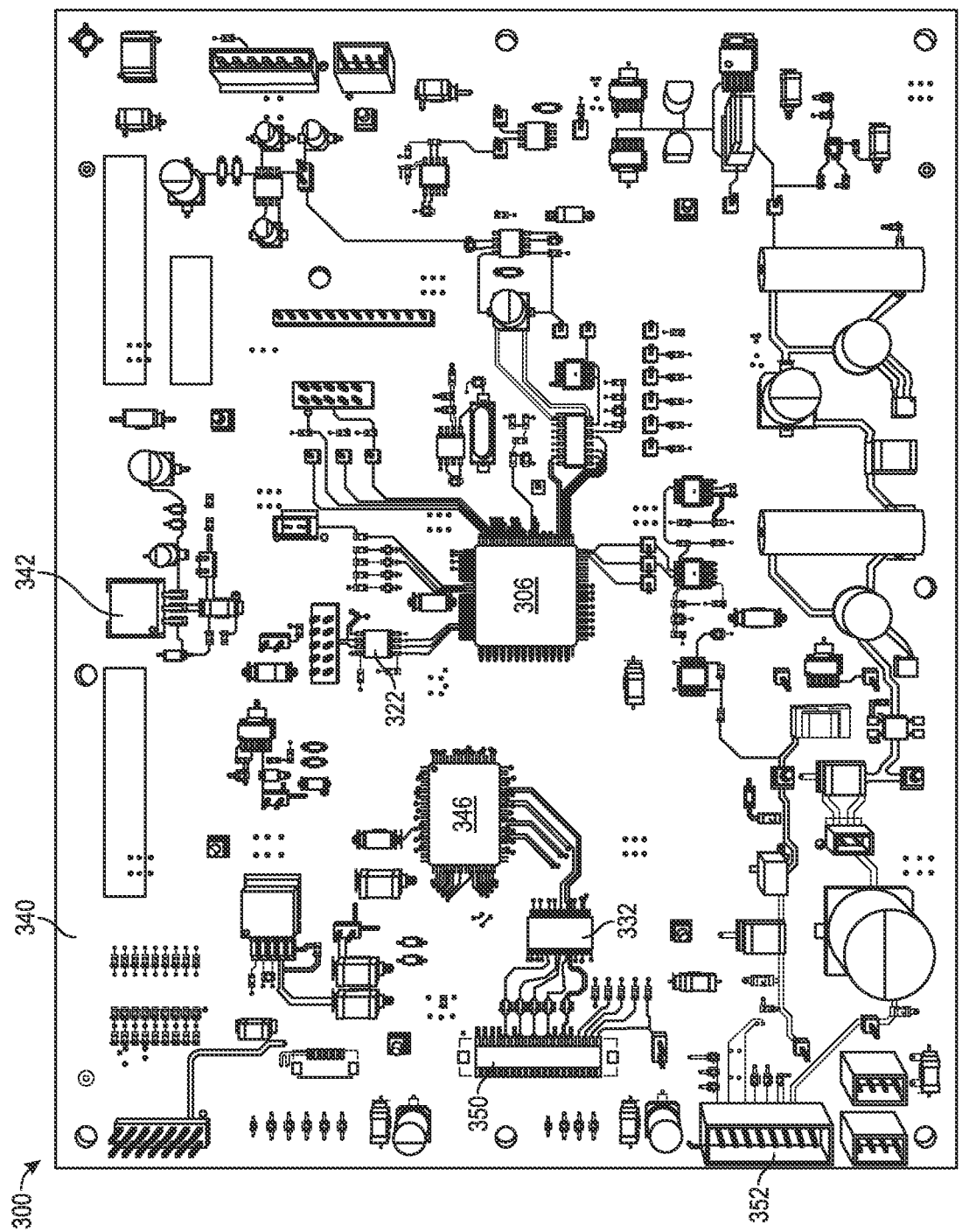
FIG. 3 illustrates a circuit board with a PLD in accordance with an embodiment.

FIG. 3 illustrates a circuit board with no software that can be used as a graphic controller for an LCD panel. In system 300, circuit board 340 includes pins, resistors, capacitors, timer 342, and other discrete and integrated electronic components.

Sensor data is input through a connector at connection 352. This data is run to a programmable logic device that has all-hardware logic gates to parse and convert values from the sensor input.

Complex programmable logic device (CPLD) or field programmable gate array (FPGA) chip 306 is the PLD that houses the hardware logic gates that control the decoding and loading of a frame buffer. PLD 306 decodes data coming from connection 352. Based on the decoded values, PLD 306 looks up addresses of bitmaps for the respective place values of numbers. The looked up addresses may be burned in the PLD logic or looked up using burned in PLD logic. For example, if a number is "20.6," PLD 306 looks up or calculates addresses for a nicely drawn bitmap of a '2,' a '0,' and a '6.'

For example, a '2' invokes logic to convert from the character (or integer) '2' to an absolute address such as 0x0200. Real world addresses, of course, may be longer and more complex. There may or may not be a mathematical calculation to arrive at the resulting memory address. If there is not a mathematical calculation, then there can be ten sets of logic gates to convert '0,' '1,' '2,' etc. to the respective memory addresses of the bitmaps.

The predefined bitmaps exist in flash memory 322. PLD 306 then copies the bitmaps from flash memory 322 to their respective x, y coordinates in SRAM frame buffer 346. For the above example, the '2' bitmap is copied to the x, y coordinate for the tens place in frame buffer 346, the '0' bitmap is copied to the ones place, and the '6' bitmap is copied to the tenths place. A decimal point bitmap is always displayed regardless of the input.

The contents of frame buffer 346 are then read out by SerDes 332 to connector 350, which leads to the LCD display.

Figure 4:
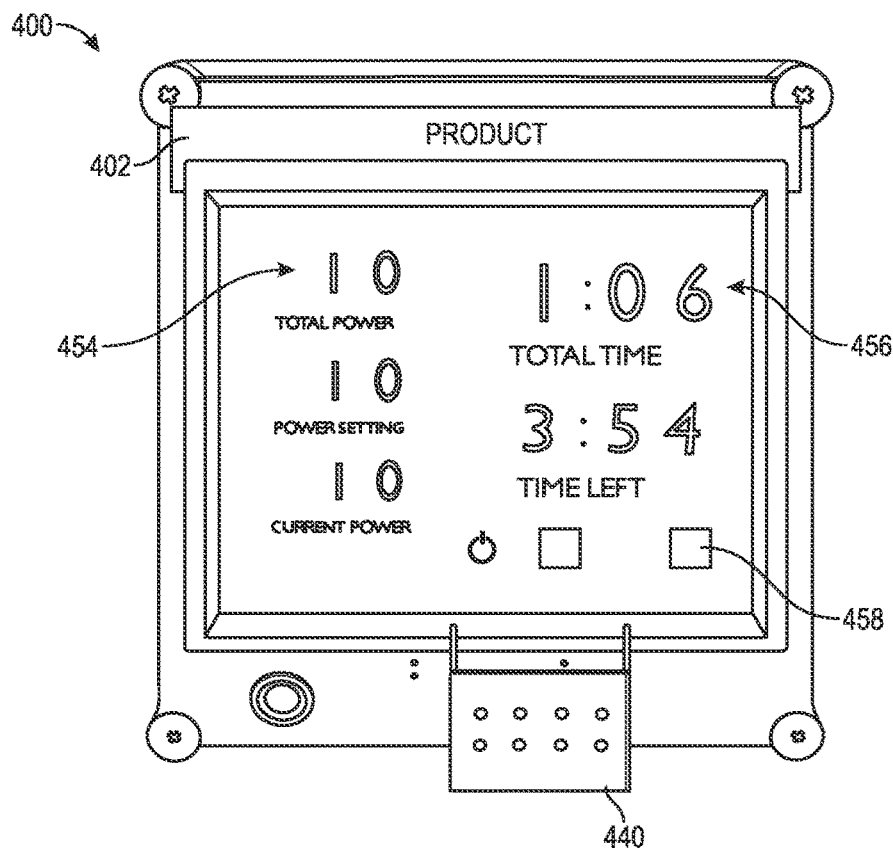
FIG. 4 illustrates a matrix liquid crystal display (LCD) panel in accordance with an embodiment.

FIG. 4 illustrates a matrix liquid crystal display (LCD) panel showing human-readable numbers and words. In system 400, matrix LCD panel 402 is a VGA resolution panel with no 7-segment or other special elements. Instead, it is purely a matrix display.

In other embodiments, mixed displays that include fixed symbols and elements as well as portions dominated by a matrix of pixels are suitable.

Multiple buttons are available to a user on pad interface 440 at the bottom of the LCD panel. The buttons can be used to control screen brightness & contrast, volume, or other interface functions. They can also be used to adjust output voltages and currents or other medical device settings.

Display 402 includes rectangular readout area 454 for showing a quantitative indication of total power. Other areas below it are set aside for a power setting and current power.

Rectangular clock area 456 shows the total time that an output current was applied. Below it is an area for time left or remaining. Special areas below the clock area are set aside for the display of alarm or warning symbols. When an alarm is triggered, one or more icons can appear or disappear in order to inform a user.

Figure 5:
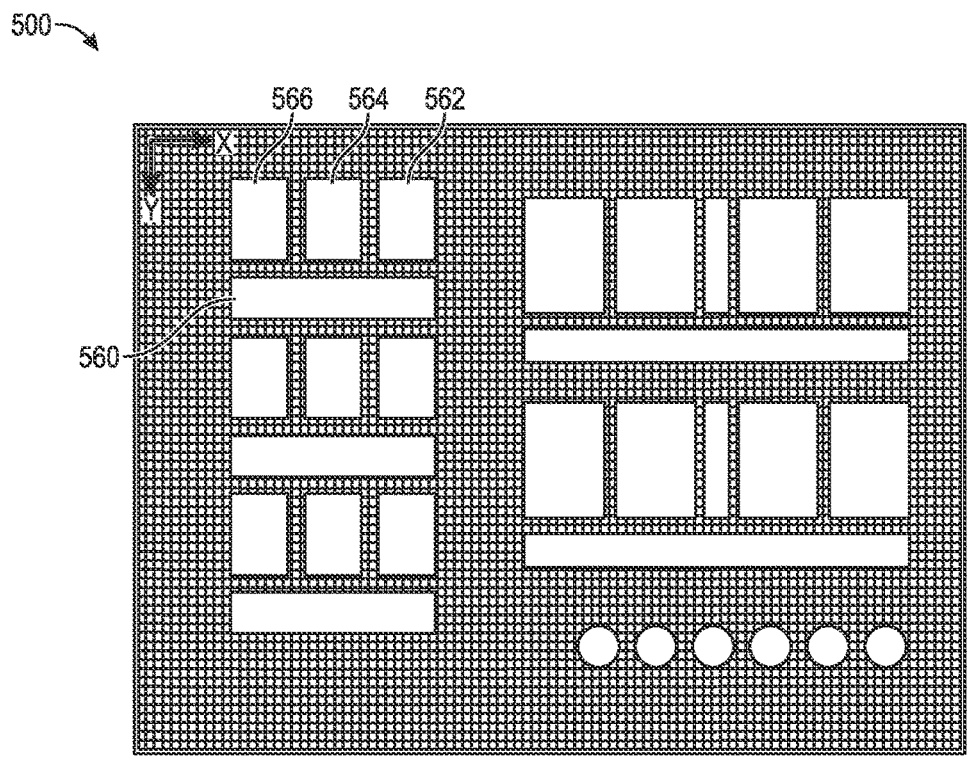
FIG. 5 illustrates screen mapping to fixed x, y coordinates on the display of FIG. 4.

FIG. 5 illustrates screen mapping to fixed x, y coordinates on the display of FIG. 4. If the frame buffer memory were laid out in x, y coordinates, it could be represented as seen in the figure.

In representation 500 there is a left side and a right side. The left side is for readouts and the right side is for clocks and alarms. Each side is colloquially called a "screen." For example, the left side can be called "Screen A," and the right side can be called "Screen B."

Three rectangular place value areas are shown at the top of the left side, each representing a place value. Area 566 is in the hundreds column, area 564 is in the tens column, and area 562 is in the ones column. Combined, the three columns can show any number between 0 and 999.

Below the columns in a broad rectangle is a bitmap area for fixed text. As seen in FIG. 4, this text simply labels the digits above it as Total Power. In other embodiments, the fixed text can be above, to the left of, or to the right of the variable numbers. There can also be areas for fixed bitmaps such as decimal points, degree symbols, units, etc. On the right side of the figure, there is an area for a fixed bitmap of a colon ':' between numbers to delimit minutes and seconds. In yet other embodiments, negative signs '−' and other bitmaps that are responsive to input values can be displayed.

Figure 6:
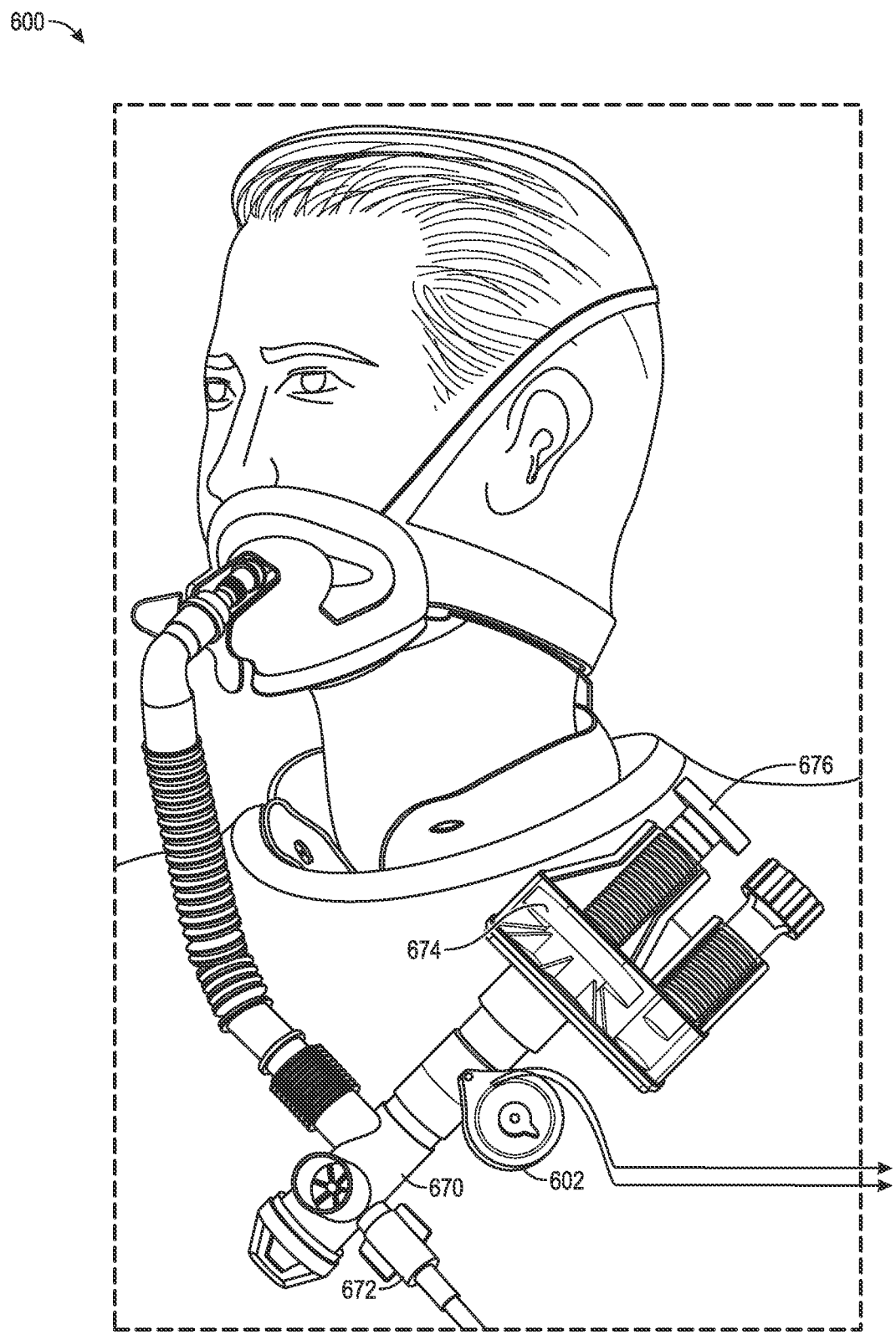
FIG. 6 is a perspective view of a ventilator in accordance with an embodiment.

FIG. 6 is a perspective view of a ventilator 600 in accordance with an embodiment. This is an exemplar use for a hardware-based display controller such as one of the embodiments shown above because there is a need for large panel displays for ventilators but only a short amount of time to certify them.

Ventilator 600 is a pneumatic valve assembly including housing 670 with input port 672 connected with a pressurized gas line. The gas line may be for pure oxygen for a patient. The housing encases diaphragm 674 whose resilient force is adjusted by adjustable knob 676.

Pressure sensor 602, which senses pressure within a lumen of housing 670, outputs voltages through wires, which is then fed to the input of the hardware-based graphical interface.

In some embodiments, a pressure sensor, filter, and carbon dioxide ($CO_2$) sensor are connected with the housing. The multiple sensors can feed into the circuit board (such as that of FIG. 3), and their values and alarms shown on a common large format LCD panel. For example, pressure readings in inches of mercury can be shown with alarms in one area of a display panel while $CO_2$ readings and an associated alarm may be shown in another area.

Other embodiments can be used for controlling electrical output. One example is a therapeutic current generator for treating hemorrhoids.

Figure 7:
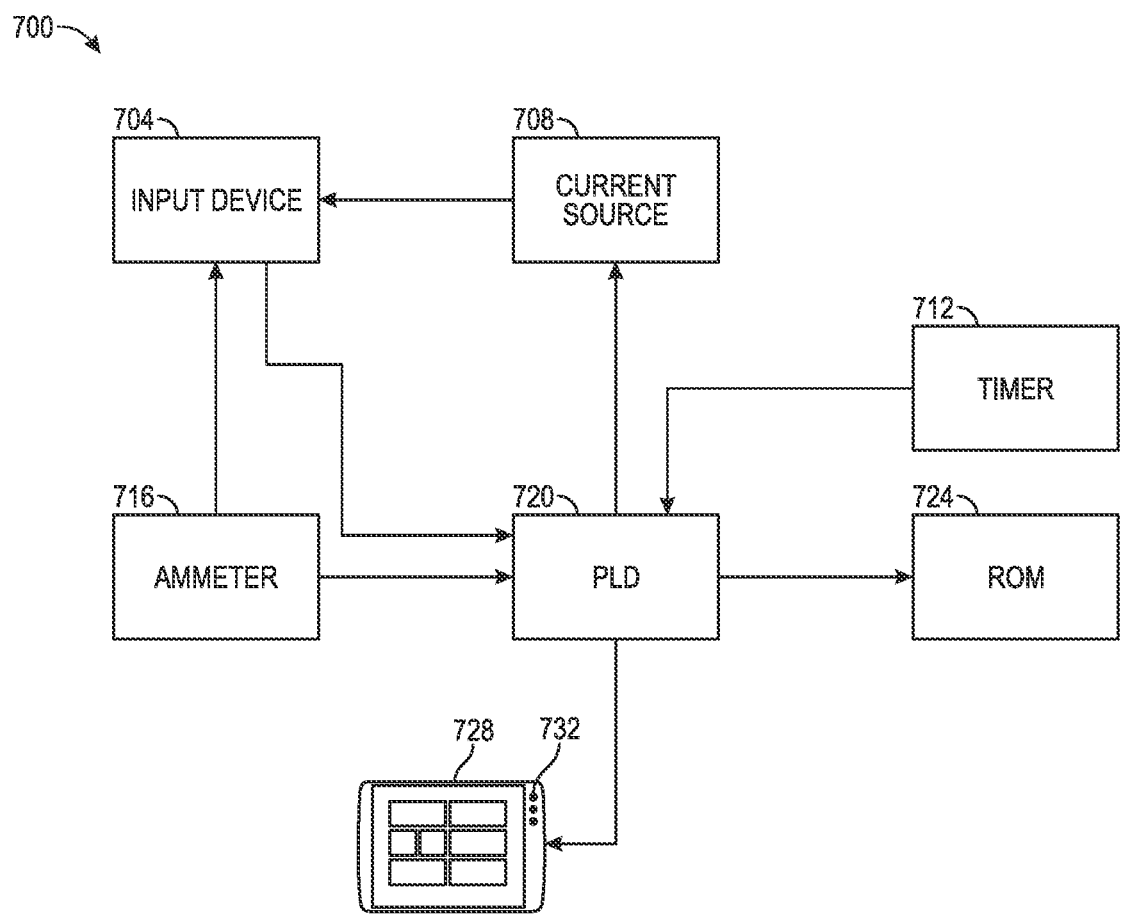
FIG. 7 illustrates a block diagram of a hardware-based graphics controller display in accordance with an embodiment.

FIG. 7 illustrates block diagram 700 a hardware-based graphics controller display in accordance with an embodiment. The graphics controller apparatus includes input device 704, current source 708, timer 712, ammeter 716, PLD 720, read-only memory (ROM) component 724, and display interface 728.

For example, input device 704 is a device that may be connected to the graphics controller apparatus via a connection port. In one embodiment, input device 704 is a surgical pencil and/or a grounding pad or return electrode which can be configured to operate with the graphics controller. In some embodiments, the input device 704 is a surgical pencil that may be configured to receive a current output supplied by the current source 708 within the graphics controller.

Current source 708 is configured to provide a negative galvanic current to the input device 704 for the treatment of hemorrhoids using hemorrhoidolysis. Current source 708 includes a conditioning circuit that is configured to generate a current output. The current output generated is a negative galvanic current between 1-25 milliamps for the use of treating hemorrhoids using hemorrhoidolysis. The conditioning circuit of the current source 708 may also be configured to output a direct current value between 1-50 milliamps while maintaining a ripple voltage at or below plus and/or minus 500 millivolts.

Ammeter 716 is configured to monitor the output of the current source 408 supplied to the input device 704. Generally, the hemorrhoidolysis procedure requires the supplement of very precise negative galvanic currents and an ammeter 716 configured to measure the output of the current source 708.

Timer 712 is included in the graphics controller. Timer 712 may be configured to record the total time negative galvanic currents have been supplied to a hemorrhoid during treatment, or the time may be configured to count down from a predetermined value. In some embodiments, timer 712 may be an individual component, or the timer 712 may be an embedded component within PLD 720. Generally, the treatment time is critical for a hemorrhoidolysis procedure, and timer 712 is configured to measure the treatment time. It will be recorded even if the time is not displayed on a graphical user interface on a display interface 728.

PLD 720 is coupled with timer 712, ammeter 716, current source 708, and input device 704. PLD 720 is also coupled with display interface 728 and memory component 724. Memory component 724 includes a read-only memory component configured to host and/or store various two-dimensional pixel representation of specific alphanumeric values such as, but not limited to, digits 0-9 and letters A-Z. These are a serious of fixed images that can be summoned by PLD 720 when required.

The memory component 724 is configured to transfer various fixed images that can be summoned by PLD 720 to be presented on display interface 728 at predetermined locations based on the fixed image addresses stored within the memory component 724. For example, the phrase "Total Time" may be stored as a fixed image in memory component 724 with a specific permanent image address that can be summoned by PLD 720 when the total time for a treatment needs to be included on the graphical user interface presented to the user on display interface 728. In some embodiments, memory component 724 will include various fixed images and various fixed image addresses that may be summoned by PLD 720 when required.

Generally, PLD 720 is the control center for the graphics controller, and PLD 720 may be configured to be coupled with and control every device and/or component coupled with PLD 720. In some embodiments, PLD 720 may include a programmable read-only memory (PROM), erasable programmable read-only memory (EPROM), electrically erasable programmable read-only memory (EEPROM), flash memory EPROM, programmable array logic, or a programmable logic array (PLA), an application specific integrated circuit (ASIC), or an application specific standard product (ASSP) which can be configured to be coupled with input device 704, current source 708, timer 712, ammeter 716, and memory component 728.

In some embodiments, the PLD may be configured to summon a specific two-dimensional pixel representation from memory component 724 based on a value read from timer 712, input device 704, current source 708, ammeter 716, display 728, or any other component and/or device coupled with PLD 720. In some embodiments, the PLD may be configured to search within the memory component 724 for a specific two-dimensional pixel representation from memory component 724 based on a value read from timer 712, input device 704, current source 708, ammeter 716, display 728, or any other component and/or device coupled with PLD 720. In some embodiments, the PLD may be configured to exhibit a specific two-dimensional pixel representation from the memory component 724 based on a value read from timer 712, input device 704, current source 708, ammeter 716, display 728, or any other component and/or device coupled with PLD 720 at a predetermined fixed address stored win memory component 724.

In some embodiments, PLD 720 may include an interrogation circuit that is configured to read an unique authentication code from an input device connected to the graphics controller. PLD 720 may be configured to store the authentication code the graphics controller has previously read from a previous input device 704 connected to the graphics controller in memory component 724. PLD 720 may further be configured to compare a current authentication codes read from a currently connected input device 704 against the stored authentication codes previously read from a previous input device 704 connected to the graphics controller. The interrogation circuit may be configured to control the current flow from current source 708 to input device 704 based on the reading of the authentication code. The authentication code may be configured to be unique for each input device 704 connected to PLD 720, or the authentication code may be configured to be unique for certain types of input device 704 and not for other types of input devices. The interrogation circuit may further be configured to prevent current source 708 from supplying a negative galvanic current to input device 704 if the authentication code read from input device 704 has been previously read, or the interrogation circuit may be configured to prevent current source 708 from supplying a negative galvanic current to input device 704 if the authentication code read from the input device has been previously read a predetermined number of times. For example, in order to prevent a doctor from using a surgical pencil on multiple patients, each surgical pencil will have its own unique identification code embedded within. When the doctor attempts to use the same surgical pencil after the graphics controller has previously read in the unique authentication code, then PLD 720 will not allow negative galvanic current to flow from the current source 708 to the surgical pencil.

Display interface 728 includes a generic screen with a predetermined display ratio. Generally, display interface 728 may be configured to present the graphical user interface generated by PLD 720 based on two-dimensional pixel representations read from memory component 724. In some embodiments, each image exhibited on the display interface 728 may be a fixed image pre-stored in the memory component 724 that is summoned by PLD 720. In some embodiments, display interface 728 may be embedded within an enclosure. In other embodiments, display interface 728 may be a separate component from the graphics controller.

In some embodiments, display interface 728 may contain at least one switch that may be activated by a doctor for the graphics controller to perform a specific action. The switch may be embedded within display interface 728, or the switch may be an independent separate component from the display interface 728. The switch 732 may include a button on an LCD screen display, a one way single pole electrical push button switch, a two way double pole electrical push button, flip, dial, or touch switch. Generally, the switch may be configured to control the amount of current supplied from current source 708 to input device 704, the amount of time associated with timer 712, or any other actions and/or functions configured by PLD 720. For example, display interface 728 may have a push button switch 732 to increase the amount of current supplied by current source 708, to decrease the current supplied, to increase the time on timer 712, to decrease the time on timer 712, to turn on or turn off the current supply, to stop, reset, or start timer 712, or for PLD 720 to read the authentication code from input device 704.

Although specific embodiments of the invention have been described, various modifications, alterations, alternative constructions, and equivalents are also encompassed within the scope of the invention. Embodiments of the present invention are not restricted to operation within certain specific environments, but are free to operate within a plurality of environments. Additionally, although method embodiments of the present invention have been described using a particular series of and steps, it should be apparent to those skilled in the art that the scope of the present invention is not limited to the described series of transactions and steps.

Further, while embodiments of the present invention have been described using a particular combination of hardware, it should be recognized that other combinations of hardware are also within the scope of the present invention.

The specification and drawings are, accordingly, to be regarded in an illustrative rather than a restrictive sense. It will, however, be evident that additions, subtractions, deletions, and other modifications and changes may be made thereunto without departing from the broader spirit and scope.

What is claimed is:

1. A hardware-based display apparatus for medical devices, the apparatus comprising:
   a sensor input;
   a matrix liquid crystal display (LCD) panel;
   a read-only memory (ROM) hosting two-dimensional, graphical bitmaps of digits 0 through 9, each bitmap stored at a predetermined, fixed memory location within the ROM;
   a programmable logic device (PLD) comprising a series of logic gates, the PLD operatively connected with the display panel and the ROM and configured to:
      automatically convert a value from the sensor input, through the series of logic gates, to at least one selected location of the ROM memory locations storing the bitmaps of digits; and
      copy the bitmap from the selected location to a random-access memory (RAM) frame buffer address corresponding to an x, y coordinate on the display panel;
   wherein the display panel is configured to show the bitmap that is copied to the RAM frame buffer address at the x, y coordinate.

2. The apparatus of claim 1 wherein automatically converting includes:
   converting the value from the sensor input to an integer or floating point number within the PLD.

3. The apparatus of claim 2 wherein the PLD is further configured to:
   compare the integer or floating point number to a threshold; and
   trigger an alarm based on the number exceeding the threshold.

4. The apparatus of claim 3 wherein the PLD is further configured to:
   copy, based on the trigger, a graphic from the ROM to a second frame buffer address corresponding to a second x, y coordinate on the display panel.

5. The apparatus of claim 3 further comprising:
   a speaker,
   wherein the PLD is further configured to sound, based on the trigger, an audible alarm through the speaker.

6. The apparatus of claim 3 further comprising:
   a timer,
   wherein the PLD is further configured to trigger the alarm based on the number exceeding the threshold over a time period clocked by the timer.

7. The apparatus of claim 1 wherein the PLD is further configured to:
   parse the value from an RS-232 serial stream, a universal serial bus (USB) data packet, or inter-integrated circuit ($I^2C$) packet from the sensor input.

8. The apparatus of claim 1 wherein the PLD is further configured to:
   convert the value from an analog voltage or analog current from the sensor input.

9. The apparatus of claim 1 further comprising:
   a sensor coupled to the sensor input.

10. An alarmed ventilator comprising:
    the hardware-based display apparatus of claim 1;
    a pneumatic valve assembly including:
       a housing with a fluidic input port configured to receive pressurized gas into the housing;
       a diaphragm within the housing;
       an adjustable knob configured to adjust force against the diaphragm; and
    a pressure sensor within the housing coupled to the sensor input,
    wherein the hardware-based display apparatus is configured to show a value from the pressure sensor.

11. The apparatus of claim 1 wherein the frame buffer address is on a static random-access memory (SRAM).

12. The apparatus of claim 1 further comprising:
    a serializer-deserializer (SerDes) configured to read from the frame buffer address and transmit pixel values to the display panel.

13. The apparatus of claim 1 wherein a frame buffer associated with the frame buffer address only addresses a subset of x, y pixel areas of the display panel.

14. The apparatus of claim 1 wherein the PLD is a programmable read-only memory (PROM), erasable programmable read-only memory (EPROM), electrically erasable programmable read-only memory (EEPROM), flash memory EPROM, field programmable gate array (FPGA), programmable array logic (PAL), programmable logic array (PLA), application specific integrated circuit (ASIC), or application specific standard product (ASSP).

15. A hardware-based graphics controller and therapeutic electric current generator apparatus comprising:
    a timer;
    a current source with a conditioning circuit and an output;
    an ammeter configured to measure the current source output;
    a liquid crystal display (LCD);
    a random-access memory (RAM) frame buffer connected with the LCD;
    a programmable logic device (PLD) comprising a series of logic gates, the PLD connected with the timer, the ammeter, and the LCD;
    a read-only memory operatively connected with the PLD, the memory hosting:
       two-dimensional pixel representations of digits 0 through 9;
       a fixed image address in the RAM frame buffer for the LCD for displaying time; and
       a permanent image address in the RAM frame buffer for the LCD for displaying current,
    wherein the PLD is configured to select, through the series of logic gates, pixel representations from the memory based on values from the timer and write the selected pixel representations starting at the fixed image address in the RAM frame buffer; and
    wherein the PLD is configured to look up pixel representations from the memory based on values from the ammeter and write the looked-up pixel representations starting at the permanent image address in the RAM frame buffer.

16. The apparatus of claim 15 further comprising:
    an interrogation circuit configured to read an authentication code from a connected device and allow current to flow from the current source only if the authentication code is legitimate.

17. The apparatus of claim 16 wherein the interrogation circuit is further configured to prevent current flowing from the current source after a predetermined number of readings of the authentication code.

18. The apparatus of claim 16 wherein the connected device is a surgical pencil or a return electrode.

19. The apparatus of claim 15 further comprising:
    a user-selectable switch for increasing or decreasing electrical current from the current source, the PLD configured to adjust the timer based on operation of the switch.

20. The apparatus of claim 15 wherein the current source and the conditioning circuit are configured to output direct current (DC) at a selected value up to 50 milliamps while keeping a ripple voltage below ±500 millivolts.

21. The apparatus of claim 20 wherein the current source and conditioning circuit are limited to output DC at a maximum of 25 milliamps,
thereby suitable for negative galvanism of hemorrhoids.

22. The apparatus of claim 15 wherein the RAM frame buffer is a static RAM (SRAM) frame buffer.

\* \* \* \* \*